US012653823B2

(12) United States Patent
Kakita

(10) Patent No.: US 12,653,823 B2
(45) **Date of Patent: *Jun. 16, 2026**

(54) PHARMACEUTICAL COMPOSITION COMPRISING 6-FLUORO-3-HYDROXY-2-PYRAZINECARBOXAMIDE OR A SALT THEREOF

(71) Applicant: FUJIFILM TOYAMA CHEMICAL CO., LTD., Chuo-ku (JP)

(72) Inventor: Kosuke Kakita, Toyama (JP)

(73) Assignee: FUJIFILM TOYAMA CHEMICAL CO., LTD., Chuo-ku (JP)

( * ) Notice: Subject to any disclaimer, the term of this patent is extended or adjusted under 35 U.S.C. 154(b) by 411 days.

This patent is subject to a terminal disclaimer.

(21) Appl. No.: 18/256,603

(22) PCT Filed: Dec. 9, 2021

(86) PCT No.: PCT/JP2021/045265

§ 371 (c)(1),
(2) Date: Jun. 8, 2023

(87) PCT Pub. No.: WO2022/131112

PCT Pub. Date: Jun. 23, 2022

(65) Prior Publication Data

US 2024/0041867 A1 Feb. 8, 2024

(30) Foreign Application Priority Data

Dec. 18, 2020 (JP) ................................ 2020-210028

(51) Int. Cl.

| | |
|---|---|
| ***A61K 31/4965*** | (2006.01) |
| ***A61K 31/167*** | (2006.01) |
| ***A61K 47/18*** | (2017.01) |
| ***A61K 47/22*** | (2006.01) |

(52) U.S. Cl.

CPC ........ *A61K 31/4965* (2013.01); *A61K 31/167* (2013.01); *A61K 47/18* (2013.01); *A61K 47/22* (2013.01)

(58) Field of Classification Search

CPC .. A61K 31/167; A61K 31/4965; A61K 47/18; A61K 47/22; A61K 9/10; A61K 9/19; A61P 31/12

See application file for complete search history.

(56) References Cited

U.S. PATENT DOCUMENTS

| | | | |
|---|---|---|---|
| 2002/0013316 A1 | 1/2002 | Furuta et al. | |
| 2012/0010221 A1 | 1/2012 | Kakuda et al. | |
| 2013/0217708 A1 | 8/2013 | Takakura et al. | |
| 2013/0274472 A1 | 10/2013 | Takakura et al. | |
| 2018/0021333 A1* | 1/2018 | Anglaret ................ | C12Q 1/701 514/255.06 |
| 2021/0059947 A1 | 3/2021 | Ono et al. | |
| 2023/0128176 A1 | 4/2023 | Ivachtchenko | |
| 2024/0041866 A1 | 2/2024 | Kakita | |

FOREIGN PATENT DOCUMENTS

| | | | |
|---|---|---|---|
| CN | 109125271 | A | 1/2019 |
| CN | 111297838 | A | 6/2020 |
| EP | 2 407 166 | A1 | 1/2012 |
| JP | 11-302162 | A | 11/1999 |
| JP | 2007-119422 | A | 5/2007 |
| JP | 2009-143922 | A | 7/2009 |
| RU | 2 731 932 | C1 | 9/2020 |
| WO | WO 00/10569 | A1 | 3/2000 |
| WO | WO 2012/043696 | A1 | 4/2012 |
| WO | WO 2012/043700 | A1 | 4/2012 |
| WO | WO 2018/003946 | A1 | 1/2018 |
| WO | WO 2019/131223 | A1 | 7/2019 |
| WO | WO 2022/131117 | A1 | 6/2022 |

OTHER PUBLICATIONS

Office Action issued Oct. 22, 2025 in Japanese Application No. 2022-569919 with Machine Translation (8 pages).
International Search Report issued Feb. 22, 2022 in PCT/JP2021/045265, filed on Dec. 9, 2021, 2 pages.
COVID-19 ni taisuru yakubutsu-chiryo no kangaekata (Japanese) (Approach to drug treatment of COVID-19), Sixth Edition, The Japanese Association for Infectious Diseases, Aug. 13, 2020, 15 pages (with English Translation).
Zhao, Yanli et al., "Favipiravir inhibits acetaminophen sulfate formation but minimally affects systemic pharmacokinetics of acetaminophen," British Journal of clinical pharmacology, vol. 80, No. 5, 2015, pp. 1076-1085, XP 071601816.
Extended European Search Report issued Oct. 29. 2024 in European Patent Application No. 21906475.5. 6 pages.

* cited by examiner

*Primary Examiner* — Sarah Pihonak

(74) *Attorney, Agent, or Firm* — Oblon, McClelland, Maier & Neustadt, L.L.P.

(57) ABSTRACT

A pharmaceutical composition comprising Components (1) and (2):
(1) 6-fluoro-3-hydroxy-2-pyrazinecarboxamide or a salt thereof; and
(2) a specific amine.

4 Claims, No Drawings

PHARMACEUTICAL COMPOSITION COMPRISING 6-FLUORO-3-HYDROXY-2-PYRAZINECARBOXAMIDE OR A SALT THEREOF

CROSS-REFERENCE TO RELATED APPLICATIONS

This application is a national stage application of PCT/JP2021/045265, filed Dec. 9, 2021 which claims priority to Japanese application JP 2020-210028, filed Dec. 18, 2020. The entire contents of both applications are incorporated herein by reference.

TECHNICAL FIELD

The present invention relates to a pharmaceutical composition comprising 6-fluoro-3-hydroxy-2-pyrazinecarboxamide (hereinafter may also be referred to as "Compound A") and an amine.

BACKGROUND ART

Compound A or a salt thereof has a superior antiviral activity and is useful as a therapeutic agent for viral infection (Patent Literature 1). Compound A has a low water solubility; however, sodium salts (Patent Literature 2) and meglumine salts (Patent Literature 3) of Compound A are known to have a relatively high solubility and be useful as a preparation for injection.

In recent years, it has been found that Compound A is also effective for novel coronavirus infection. According to Non Patent Literature 1, the dose of Compound A for novel coronavirus infection is a total of 18,000 mg (3600 mg [1800 mg BID] on Day 1+1600 mg [800 mg BID] on Days 2 to 10) administered over 10 days. This is twice higher than the dose for influenza, which is a total of 8000 mg (3200 mg [1600 mg BID] on Day 1+1200 mg [600 mg BID] on Days 2 to 5).

CITATION LIST

Patent Literature

[Patent Literature 1]
International Publication No. WO 00/10569
[Patent Literature 2]
International Publication No. WO 2012/043700
[Patent Literature 3]
International Publication No. WO 2012/043696

Non Patent Literature

[Non Patent Literature 1]
COVID-19 ni taisuru yakubutsu-chiryo no kangaekata (Japanese) (Approach to drug treatment of COVID-19), Sixth Edition, The Japanese Association for Infectious Diseases, p. 5 and 6

SUMMARY OF INVENTION

Technical Problem

When Compound A is used for the treatment of novel coronavirus infection, a dose increase of Compound A is expected. If the solubility of Compound A which is used as a liquid preparation, such as a preparation for injection or a syrup, can be made higher than that of a sodium salt or a meglumine salt of Compound A (i.e., obtaining a high concentration aqueous solution of Compound A), it will be convenient from viewpoints of a storage space for the preparation and administration to patients. The object of the present invention is to provide a pharmaceutical composition with further improved solubility of Compound A.

Solution to Problem

As a result of extensive studies to achieve the above-mentioned object, the present inventors found that a pharmaceutical composition in which the above-mentioned object was achieved could be provided by using Compound A in combination with a specific amine, and thus the present invention was accomplished.

One aspect of the present invention is described below.

<1>

A pharmaceutical composition comprising Components (1) and (2):

(1) 6-fluoro-3-hydroxy-2-pyrazinecarboxamide or a salt thereof; and (2) an amine, the amine being selected from an amine represented by general formula [1], an amine represented by general formula [2], an amine represented by general formula [3], DABCO, lidocaine, pyrrole, pyridine, imidazole, pyrazole, oxazole, thiazole, imidazoline, thiazine, triazole, tetrazole, pyridazine, pyrimidine, pyrazine, indole, isoindole, benzoimidazole, purine, benzotriazole, quinoline, isoquinoline, quinazoline, quinoxaline, cinnoline, pteridine, anthracene, and carbazole:

[Formula 1]

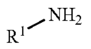

[1]

wherein $R^1$ represents a $C_{3-6}$ alkyl group that may be substituted with a hydroxy group or a thiol group,

[Formula 2]

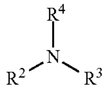

[2]

wherein $R^2$ and $R^3$, which are identical to or different from each other, represent a $C_{1-6}$ alkyl group that may be substituted with a hydroxy group or a thiol group, and $R^4$ represents a hydrogen atom or a $C_{1-5}$ alkyl group that may be substituted with a hydroxy group or a thiol group,

[Formula 3]

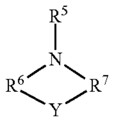

[3]

wherein Rh represents a hydrogen atom or a $C_{1-5}$ alkyl group that may be substituted with a hydroxy group or a thiol group, $R^6$ and $R^7$, which are identical to or different from each other, represent a $C_{1-5}$ alkylene group that may be substituted with a hydroxy group or a thiol group, and Y represents an atomic bonding, an oxygen atom, a sulfur atom, or NH.

<2>

The pharmaceutical composition according to <1>, wherein the amine is selected from the following compound group:

a compound group consisting of isopropylamine, propanolamine, diethanolamine, diisopropanolamine, triisopropanolamine, triethanolamine, ethyldiethanolamine, triethylamine, Bis-Tris, DABCO, lidocaine, pyrrole, pyridine, imidazole, pyrazole, oxazole, triazole, imidazoline, thiazine, triazole, tetrazole, pyridazine, pyrimidine, pyrazine, indole, isoindole, benzoimidazole, purine, benzotriazole, quinoline, isoquinoline, quinazoline, quinoxaline, cinnoline, pteridine, anthracene, and carbazole.

<3>

The pharmaceutical composition according to <1> or <2>, comprising 0.2 equivalents or more of an amine to 6-fluoro-3-hydroxy-2-pyrazinecarboxamide or a salt thereof.

<4>

The pharmaceutical composition according to any of <1> to <3>, which further comprises Component (3) and is an aqueous solution:

(3) water.

<5>

The pharmaceutical composition according to <4>, wherein the concentration of 6-fluoro-3-hydroxy-2-pyrazinecarboxamide or a salt thereof is 100 mg/mL or higher.

<6>

The pharmaceutical composition according to <1> to <3>, which is a lyophilized preparation.

Advantageous Effect of Invention

According to the present invention, a pharmaceutical composition that is capable of containing a high concentration of Compound A in water is provided.

DESCRIPTION OF EMBODIMENTS

In the present specification, the range of numerical values expressed using "to" means a range inclusive of numerical values written before and after "to" as a minimum value and a maximum value, respectively. In one aspect, the value itself of one of a minimum value and a maximum value or both may be excluded (that is, the range can mean "more than x" and "less than x" instead of "x or more" and "x or less").

In the present specification, when a plurality of substances corresponding to each component exist in the composition, the amount of each component in the composition means the total amount of the plurality of substances in the composition, unless otherwise specified.

In the present specification, each term has the following meaning, unless otherwise specified.

The term "$C_{3-6}$ alkyl group" means, for example, a linear or branched chain alkyl group having three to six carbon atoms, such as propyl group, isopropyl group, butyl group, sec-butyl group, isobutyl group, tert-butyl group, pentyl group, isopentyl group, or hexyl group.

The term "$C_{1-5}$ alkyl group" means, for example, a linear or branched chain alkyl group having one to five carbon atoms, such as methyl group, ethyl group, propyl group, isopropyl group, butyl group, sec-butyl group, isobutyl group, tert-butyl group, pentyl group, or isopentyl group.

<Compound A>

In the present invention, Compound A (6-fluoro-3-hydroxy-2-pyrazinecarboxamide) or a salt thereof is used as an active ingredient. A salt can be any pharmaceutically acceptable salt and is preferably a sodium salt or a meglumine salt.

If Compound A has isomers (e.g., an optical isomer, a geometric isomer, and a tautomer), the present invention encompasses all the isomers, as well as hydrates, solvates, and all crystalline forms.

<Amine>

An amine used in the present invention can be any amine that can improve the water solubility of Compound A (i.e., function as a solubilizer) when it is used in combination with Compound A. The degree of improvement of solubility is not particularly limited, and the amine is preferably an amine that improves the water solubility of Compound A 1.4-fold or more, more preferably an amine that improves it two-fold or more, yet more preferably an amine that improves it 2.5-fold or more, as compared with a sodium salt or a meglumine salt of Compound A. One or more different amines can be used in admixture with each other. The amine can also be used in combination with an inorganic base such as sodium hydroxide or an amino sugar such as meglumine.

The structure of an amine is not particularly limited, and an amine represented by general formula [1] is preferred. In the amine represented by general formula [1], $R^1$ is preferably a propyl group, an isopropyl group, a 2-hydroxypropyl group, a 3-hydroxypropyl group, a sec-butyl group, an isobutyl group, or a Cert-butyl group, more preferably a 2-hydroxypropyl group or an isopropyl group. When $R^1$ is substituted with a hydroxy group or a thiol group, having one substituent group is preferred.

As another aspect, an amine is preferably an amine represented by general formula [2]. In the amine represented by general formula [2], $R^2$ and $R^3$, which are identical to or different from each other, are preferably a methyl group, an ethyl group, a propyl group, an isopropyl group, a butyl group, an isobutyl group, a Cert-butyl group, a 1-hydroxyethyl group, a 2-hydroxyethyl group, a 1-hydroxypropyl group, a 2-hydroxypropyl group, a 3-hydroxypropyl group, or a tris(hydroxymethyl)methyl group, more preferably an ethyl group, a 2-hydroxyethyl group, a 2-hydroxypropyl group, or a tris(hydroxymethyl)methyl group; and $R^4$ is preferably a hydrogen atom, a methyl group, an ethyl group, a propyl group, an isopropyl group, a butyl group, an isobutyl group, a Cert-butyl group, a 1-hydroxyethyl group, a 2-hydroxyethyl group, a 1-hydroxypropyl group, a 2-hydroxypropyl group, a 3-hydroxypropyl group, or a tris(hydroxymethyl)methyl group, more preferably a hydrogen atom, an ethyl group, a 2-hydroxyethyl group, or a tris(hydroxymethyl)methyl group.

When $R^2$, $R^3$, or $R^4$ is substituted with a hydroxy group or a thiol group, having one substituent group for each alkyl group is preferred.

The amine represented by general formula [2] is preferably diethylamine, dipropylamine, diisopropylamine, dibutylamine, diisobutylamine, di-tert-butylamine, trimethylamine, triethylamine, tripropylamine, triisopropylamine, tributylamine, triisobutylamine, tri-tert-butylamine, diethanolamine, diisopropanolamine, triisopropanolamine, triethanolamine, methyldiethanolamine, ethyldiethanolamine, or bis(2-hydroxyethyl)iminotris(hydroxymethyl)methane (Bis-Tris), more preferably triethylamine, diethanolamine, diisopropanolamine, triethanolamine, ethyldiethanolamine, or Bis-Tris.

As another aspect, an amine is preferably an amine represented by general formula [3]. In the amine represented by general formula [3],

- $R^5$ is preferably a hydrogen atom, a methyl group, an ethyl group, or a hydroxymethyl group, more preferably a hydrogen atom;
- $R^6$ and $R^7$, which are identical to or different from each other, are preferably a methylene group, an ethylene group, or a propylene group, more preferably an ethylene group; and
- Y is preferably an atomic bonding, an oxygen atom, or NH.

The amine represented by general formula [3] is preferably pyrrolidine, piperidine, piperazine, or morpholine.

As another aspect, an amine is preferably isopropylamine, propanolamine, diethanolamine, diisopropanolamine, triisopropanolamine, triethanolamine, ethyldiethanolamine, triethylamine, Bis-Tris, 1,4-diazabicyclo[2.2.2]octane (DABCO), lidocaine, pyrrole, pyridine, imidazole, pyrazole, oxazole, triazole, imidazoline, thiazine, triazole, tetrazole, pyridazine, pyrimidine, pyrazine, indole, isoindole, benzoimidazole, purine, benzotriazole, quinoline, isoquinoline, quinazoline, quinoxaline, cinnoline, pteridine, anthracene, or carbazole.

The amount of an amine used is not particularly limited as long as the amount improves the water solubility of Compound A, and is preferably 0.2 equivalents or more to Compound A, more preferably 0.2 to 10 equivalents, yet more preferably 0.3 to 5 equivalents, yet more preferably 0.4 to 2 equivalents, particularly preferably 0.5 to 1 equivalents.

An amine can be manufactured by methods known per se or by using these methods in combination, or a commercially available product can be used.

<Water>

Water used in the present invention is not particularly limited as long as it is suitable for manufacture of a pharmaceutical composition and is preferably purified water, water of a grade equivalent to or higher than purified water, or water for injection.

<Pharmaceutical Composition>

In addition to a composition obtained by dissolving Compound A or a salt thereof together with an amine in water (i.e., a liquid preparation), the pharmaceutical composition of the present invention includes a composition obtained by lyophilizing the liquid preparation (i.e., a lyophilized preparation). Both a liquid preparation and a lyophilized preparation can be used as a preparation for injection, a syrup, or the like. When Compound A is used as a liquid preparation, the concentration of Compound A is preferably 100 mg/mL or higher, more preferably 200 mg/mL or higher.

[Method for Manufacturing Liquid Preparation]

Step (1):

An aqueous solution of Compound A is prepared by dissolving Compound A or a salt thereof together with an amine in water. The expression "together with an amine" means that Compound A and an amine may be added to water simultaneously, or either component may be added to water first, followed by addition of the remaining component.

Step (2):

The aqueous solution obtained in Step (1) is filled into a drug product container (e.g., a vial), and then the container is sealed to obtain a liquid preparation. Step (1) and Step (2) may be performed simultaneously. That is, a liquid preparation may be obtained by directly preparing an aqueous solution of Compound A in a drug product container.

[Method for Manufacturing Lyophilized Preparation]

Step (1):

Compound A or a salt thereof is dissolved together with an amine in water to prepare an aqueous solution of Compound A. The expression "together with an amine" means that Compound A and an amine may be added to water simultaneously, or either component may be added to water first, followed by addition of the remaining component.

Step (2):

The aqueous solution obtained in Step (1) is filled into a drug product container (e.g., a vial). Step (1) and Step (2) may be performed simultaneously. That is, an aqueous solution of Compound A may be directly prepared in a drug product container.

Step (3):

The aqueous solution obtained in Step (1) is lyophilized by a usual lyophilization method. The order of Step (2) and Step (3) is not limited. That is, these steps are performed as follows:

Step (3) following Step (2):

The aqueous solution filled into a drug product container at Step (2) is lyophilized at Step (3).

Step (2) following Step (3):

The aqueous solution obtained in Step (1) is lyophilized at Step (3), and then the lyophilized preparation is filled into a drug product container at Step (2).

Step (4):

The drug product container, in which a lyophilized solution obtained at Steps (2) and (3) is filled, is sealed to obtain a lyophilized preparation.

[Administration of Pharmaceutical Composition]

The administration method, dose, and number of doses of the pharmaceutical composition of the present invention can be suitably selected depending on patient's age, body weight, and symptom. Usually, the amount that can exhibit a drug effect may be divided into one to several doses per day and intramuscularly or intravenously injected or orally administered.

<Other Additives>

To the pharmaceutical composition of the present invention, an osmotic pressure regulator, a pH regulator, a buffer, a stabilizer, a surfactant, a soothing agent, a sweetener and/or a preservative, and the like which are commonly used may be added as necessary.

Examples of an osmotic pressure regulator include sodium chloride, glycerin, and propylene glycol.

Examples of a pH regulator and/or a buffer include acids such as hydrochloric acid, phosphoric acid, sulfuric acid, methanesulfonic acid, acetic acid, lactic acid, maleic acid, citric acid, tartaric acid, ascorbic acid, and benzoic acid; salts such as sodium hydrogen carbonate, sodium carbonate, sodium dihydrogen phosphate, potassium dihydrogen phosphate, disodium hydrogen phosphate, dipotassium hydrogen phosphorate, trisodium phosphate, disodium citrate, sodium deoxycholate, and sodium sulfite; and bases such as sodium hydroxide, trometamol, monoethanolamine, diethanolamine, triethanolamine, L-arginine, and L-lysine.

Examples of a stabilizer include sodium hydrogen sulfite, sodium pyrosulfite, potassium pyrosulfite, sodium pyrophosphate, sodium thiosulfate, sodium metasulfobenzoate, sodium formaldehyde sulfoxylate, ethylenediamine, sodium edetate, thioglycolic acid, sodium gluconate, monopotassium L-glutamate, L-lysine L-glutamate, sodium chondroitin sulfate, albumin, L-aspartic acid, L-cysteine, and dibutylated hydroxytoluene.

Examples of a surfactant include a sorbitan fatty acid ester, polyoxyethylene hydrogenated castor oil, polyoxyethylene sorbitan monolaurate, polyoxyethylene polyoxypropylene glycol, and polysorbate.

Examples of a soothing agent include lidocaine, procaine, meprylcaine, and benzyl alcohol.

Examples of a preservative include cresol, phenol, methyl paraoxybenzoate, ethyl paraoxybenzoate, benzalkonium chloride, and benzethonium chloride.

Examples of a sweetener include fructose, glucose, liquid sugar, honey, erythritol, xylitol, saccharin, sucralose, aspartame, and acesulfame potassium.

EXAMPLES

The present invention is described in more detail below using the following Test Examples and Examples. However, the present invention is not limited to these examples.

Test Example 1: Solubility

To examine the solubilizing effect of an amine, Compound A was suspended in water, 1 equivalent of an amine to a compound or an aqueous solution thereof was added, and the mixture was stirred at room temperature for two hours or longer. Subsequently, the mixture was filtered through a filter with a pore size of 0.45 μm, and the concentration of the filtrate was measured. The results are shown in Table 1. It should be noted that Compound A was completely dissolved in Examples 1, 3, 4, 5, 7, 10, and 11.

TABLE 1

| Example number | Amine or base | Solubility (mg/mL) |
|---|---|---|
| Example 1 | Diethanolamine | >268 |
| Example 2 | Triethanolamine | 340 |
| Example 3 | Diisopropanolamine | >264 |
| Example 4 | N-Ethyldiethanolamine | >271 |
| Example 5 | Triethylamine | >267 |
| Example 6 | Triisopropanolamine | 266 |
| Example 7 | DABCO | >311 |
| Example 8 | Lidocaine | 169 |
| Example 9 | Bis-Tris | 133 |
| Example 10 | Propanolamine | >229 |
| Example 11 | Isopropylamine | >219 |
| Comparative Example 1 | Sodium hydroxide | 99 |
| Comparative Example 2 | Meglumine | 87 |

Example 1

To a suspension of 1500 mg of Compound A in 2.49 mL of water, 2.51 g of 40% (w/w) aqueous solution of diethanolamine was added, and the solubility was measured by the method shown in Test Example 1.

Example 2

To a suspension of 500 mg of Compound A in 0.29 mL of water, 1.21 g of 40% (w/w) aqueous solution of triethanolamine was added, and the solubility was measured by the method shown in Test Example 1.

Example 3

To a suspension of 1500 mg of Compound A in 1.82 mL of water, 3.18 g of 40% (w/w) aqueous solution of diisopropanolamine was added, and the solubility was measured by the method shown in Test Example 1.

Example 4

To a suspension of 1500 mg of Compound A in 1.82 mL of water, 3.18 g of 40% (w/w) aqueous solution of ethyldiethanolamine was added, and the solubility was measured by the method shown in Test Example 1.

Example 5

To a suspension of 1500 mg of Compound A in 4.03 mL of water, 0.97 g of triethylamine was added, and the solubility was measured by the method shown in Test Example 1.

Example 6

To a suspension of 500 mg of Compound A in 1.5 mL of water, 0.62 g of triisopropanolamine was added, and the solubility was measured by the method shown in Test Example 1.

Example 7

To a suspension of 500 mg of Compound A in 1.5 mL of water, 0.36 g of DABCO was added, and the solubility was measured by the method shown in Test Example 1.

Example 8

To a suspension of 500 mg of Compound A in 1.5 mL of water, 0.76 g of lidocaine was added, and the solubility was measured by the method shown in Test Example 1.

Example 9

To a suspension of 500 mg of Compound A in 1.5 mL of water, 0.68 g of Bis-Tris was added, and the solubility was measured by the method shown in Test Example 1.

Example 10

To a suspension of 500 mg of Compound A in 1.5 mL of water, 0.24 g of propanolamine was added, and the solubility was measured by the method shown in Test Example 1.

Example 11

To a suspension of 500 mg of Compound A in 1.5 mL of water, 0.28 mL of isopropylamine was added, and the solubility was measured by the method shown in Test Example 1.

Comparative Example 1

To a suspension of 500 mg of Compound A in 4 mL of water, 0.13 g of sodium hydroxide was added, and the solubility was measured by the method shown in Test Example 1.

Comparative Example 2

To a suspension of 500 mg of Compound A in 4 mL of water, 0.64 g of meglumine was added, and the solubility was measured by the method shown in Test Example 1.

All examples were shown to improve the solubility of Compound A in water as compared with a sodium salt (Comparative Example 1) or a meglumine salt (Comparative Example 2). In particular, triethanolamine in Example 2 showed excellent solubility which is equivalent to or higher than Comparative Example, even when 0.5 equivalents of triethanolamine was added.

The invention claimed is:

1. A pharmaceutical composition comprising Components (1) and (2):

(1) 6-fluoro-3-hydroxy-2-pyrazinecarboxamide or a salt thereof; and (2) 0.2 equivalents or more of an amine to Component (1), wherein the amine is selected from diisopropanolamine, n-ethyldiethanolamine, triisopropanolamine, DABCO, and propanolamine.

2. The pharmaceutical composition of claim 1, which further comprises Component (3) and is an aqueous solution:

(3) water.

3. The pharmaceutical composition according to claim 2, wherein the concentration of 6-fluoro-3-hydroxy-2-pyrazinecarboxamide or a salt thereof is 100 mg/mL or higher.

4. The pharmaceutical composition of claim 1, which is a lyophilized preparation.

* * * * *